United States Patent
Dai (10) Patent No.: US 10,495,240 B2
(45) Date of Patent: Dec. 3, 2019

(54) WEAR-RESISTANT MULTI-LAYER RETRACTABLE WATER PIPE

(71) Applicant: Songlin Dai, Taizhou (CN)

(72) Inventor: Songlin Dai, Taizhou (CN)

(73) Assignee: Zhejiang Helen Plastic Co., Ltd., Taizhou, Zhejiang Province (CN)

( * ) Notice: Subject to any disclaimer, the term of this patent is extended or adjusted under 35 U.S.C. 154(b) by 0 days.

(21) Appl. No.: 15/957,877

(22) Filed: Apr. 19, 2018

(65) Prior Publication Data
US 2019/0323636 A1    Oct. 24, 2019

(51) Int. Cl.
| | |
|---|---|
| *F16L 11/00* | (2006.01) |
| *F16L 11/118* | (2006.01) |
| *B32B 3/28* | (2006.01) |
| *B32B 5/02* | (2006.01) |
| *B32B 9/02* | (2006.01) |
| *B32B 9/04* | (2006.01) |
| *B32B 25/10* | (2006.01) |
| *B32B 27/12* | (2006.01) |
| *C25B 1/04* | (2006.01) |
| *C25B 9/06* | (2006.01) |
| *A01N 59/00* | (2006.01) |
| *F16L 11/11* | (2006.01) |
| *B32B 1/08* | (2006.01) |

(52) U.S. Cl.
CPC ............ *F16L 11/118* (2013.01); *A01N 59/00* (2013.01); *B32B 1/08* (2013.01); *B32B 3/28* (2013.01); *B32B 5/024* (2013.01); *B32B 9/025* (2013.01); *B32B 9/047* (2013.01); *B32B 25/10* (2013.01); *B32B 27/12* (2013.01); *C25B 1/04* (2013.01); *C25B 9/06* (2013.01); *F16L 11/11* (2013.01); *B32B 2250/03* (2013.01); *B32B 2262/02* (2013.01); *B32B 2262/062* (2013.01); *B32B 2262/08* (2013.01); *B32B 2307/5825* (2013.01); *B32B 2597/00* (2013.01)

(58) Field of Classification Search
CPC ........... F16L 11/111; F16L 11/11; F16L 11/04
USPC ........................................ 138/118, 119, 109
See application file for complete search history.

(56) References Cited

U.S. PATENT DOCUMENTS

| | | | | |
|---|---|---|---|---|
| 4,009,734 A | * | 3/1977 | Sullivan | .................. B29C 53/12 138/118 |
| 6,523,539 B2 | * | 2/2003 | McDonald | ............... A62B 7/14 128/205.25 |
| 6,955,189 B1 | * | 10/2005 | Weyker | .................. F16L 11/121 138/104 |
| 9,127,791 B2 | * | 9/2015 | Ragner | .................. F16L 11/118 |

(Continued)

*Primary Examiner* — Patrick F Brinson (57) ABSTRACT

A wear-resistant multi-layer retractable water pipe, comprising a retractable inner pipe; a one- or multi-layer retractable fabric sleeve; and a retractable wear-resistant protective layer, wherein the retractable inner pipe is nested in the fabric sleeve, and the fabric sleeve is nested in the retractable wear-resistant protective layer. The present disclosure has the following advantages: the pressure bearing capacity of the water pipe is improved; second, the fabric sleeve is not easily worn and scratched, and the service life of the water pipe is prolonged; even if the inner pipe is broken, the outermost wear-resistant protective layer has a certain pressure resistance, ensuring that the water pipe can continue to be used, the service life of the water pipe is prolonged; and, the outermost wear-resistant protective layer has a smooth surface and therefore is easy to clean.

8 Claims, 8 Drawing Sheets

(56) References Cited

U.S. PATENT DOCUMENTS

| | | | |
|---|---|---|---|
| 9,371,944 B2* | 6/2016 | Ragner | F16L 11/118 |
| 9,964,239 B2* | 5/2018 | Disbrow | F16L 11/12 |
| 2013/0213514 A1* | 8/2013 | Berardi | F16L 11/00 |
| | | | 138/109 |
| 2016/0312928 A1* | 10/2016 | Blanchette | F16L 11/10 |

* cited by examiner

WEAR-RESISTANT MULTI-LAYER RETRACTABLE WATER PIPE

TECHNICAL FIELD

The present disclosure belongs to the technical field of retractable water pipes, and in particular relates to a wear-resistant multi-layer retractable water pipe.

BACKGROUND

In general, water pipes are needed for household car washing or garden watering. At present, retractable pipes have been very popular. However, ordinary retractable water pipes are not durable with a short service life and have the following shortcomings: first, the outermost fabric sleeve is prone to wear or tear during use, and furthermore, sharp gravel particles and plant prickles on the ground can pierce the fabric sleeve, so that the pressure-resistant effect of the fabric sleeve is lost, causing that the inner pipe is expanded and ruptured from the rupture of the fabric sleeve; second, with the broken of the outermost fabric sleeve, the gravel particles and the plant prickles can directly contact the inner pipe, leading to the rupture of the inner pipe; third, the fabric sleeve is easily contaminated with muddy water and dust when wriggling on the ground, which is not conducive to its cleaning and storage.

SUMMARY

The purpose of the present disclosure is to provide a wear-resistant multi-layer retractable water pipe with good wear resistance, a long service life and easy cleaning.

The object of the present disclosure is achieved by a wear-resistant multi-layer retractable water pipe, comprising: a retractable inner pipe; a fabric sleeve, configured as a one- or multi-layer retractable fabric sleeve; and a retractable wear-resistant protective layer, wherein the retractable inner pipe is nested in the fabric sleeve, and the fabric sleeve is nested in the retractable wear-resistant protective layer.

The fabric sleeve is a corrugated sleeve forming a plurality of peaks (i.e. top points in a direction oriented towards the wear-resistant protective layer) and a plurality of valleys (i.e. bottom points in a direction oriented towards the inner pipe). The valleys of the fabric sleeve are axially slidable on an outer surface of the inner pipe when the fabric sleeve is deployed or retracted.

The wear-resistant protective layer can be deployed or retracted as along with the deployment or retraction of the fabric sleeve.

In the case of the corrugated fabric sleeve, the peaks of the fabric sleeve are further fit with an inner wall surface of the wear-resistant protective layer.

An inner wall surface of the wear-resistant protective layer is fit with an outer surface of the fabric sleeve.

Two ends of the water pipe are connected to a pipe fitting, on which two ends of the inner pipe, of the fabric sleeve, and of the wear-resistant protective layer are respectively fixed.

The inner pipe is made of at least one retractable material selected from latex, silica gel, TPE (Thermoplastic Elastomer), TPR (Thermoplastic Rubber), TPU (Thermoplastic polyurethane) and TPX (Transparent Polymer X, high-crystallized transparent plastic).

The fabric sleeve is a corrugated or straight cylindrical fabric sleeve woven with chemical fiber threads, cotton threads or silk threads.

The wear-resistant protective layer is made of a retractable plastic material or leather material.

Compared with the prior art, the present disclosure has the following prominent and beneficial technical effects.

Since the outer side of the fabric sleeve is sleeved with the wear-resistant protective layer, it can be effectively prevented that the fabric sleeve is easily worn directly during its wriggling, that the fabric sleeve and the inner pipe are easily scratched and pierced, and that the gravel particles and the plant prickles are brought between the inner pipe and the fabric sleeve or onto the surface of the fabric sleeve, so that the service life of the entire retractable water pipe is prolonged.

A wear-resistant protective layer is added on the outermost layer, and the intermediate pressure-resistant fabric sleeve is configured as a one- or multi-layer structure, so that the pressure resistance of the entire retractable water pipe is substantially improved and thus the service life of the retractable water pipe is prolonged.

The inner pipe, the fabric sleeve and the wear-resistant protective layer are retractable synchronously with the change of the water pressure, correspondingly reducing the mutual wear among the three layers of materials and prolonging the service life.

Even if the inner pipe is broken due to various reasons and the water within the pipe passes through the fabric sleeve, a new water flow channel can be formed between the inner pipe and the wear-resistant protective layer, and therefore the water pipe can continue to be used, until the outmost wear-resistant protective layer is ruptured. Accordingly, the service life of the retractable water pipe is greatly prolonged.

The fabric sleeve is configured as a one- or multi-layer corrugated or straight cylindrical retractable fabric sleeve. The contacting area of the corrugated fabric sleeve with the inner pipe is small and thus generates a low axial frictional force onto the outer surface of the inner pipe, so that the damage to the inner pipe caused by the friction is reduced.

The wear-resistant protective layer is not only wear-resistant and retractable, but also has a smooth surface not prone to catch muddy water and dust. Actually, the wear-resistant protective layer is easy to clean even if it is contaminated with a small amount of muddy water and dust, and it has a convenient storage.

The present disclosure is widely applicable to car washing, garden watering, home cleaning and other occasions.

DETAILED DESCRIPTION

The present disclosure will be further described in detail below with reference to the accompanying drawings.

Figure 1:
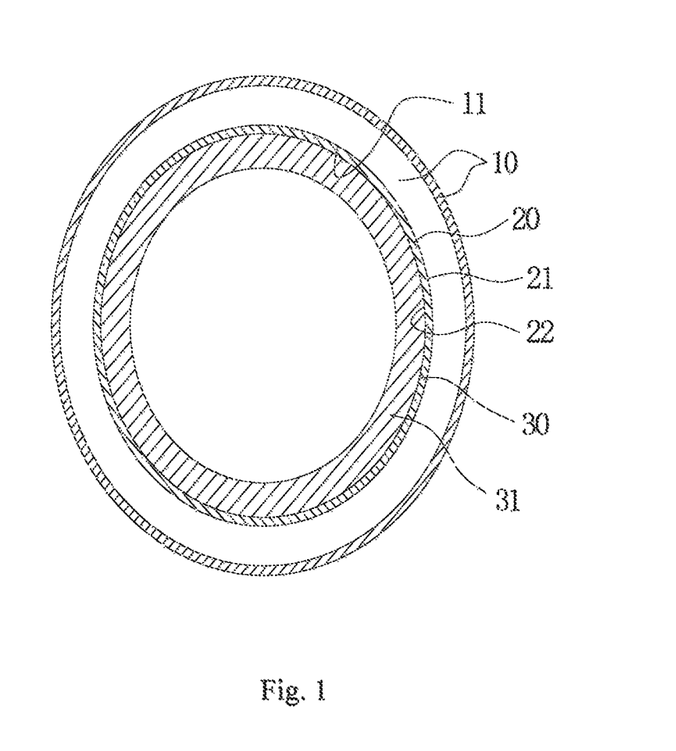
FIG. 1 is a transverse sectional view of the water pipe according to one embodiment of the present disclosure.
Figure 2:
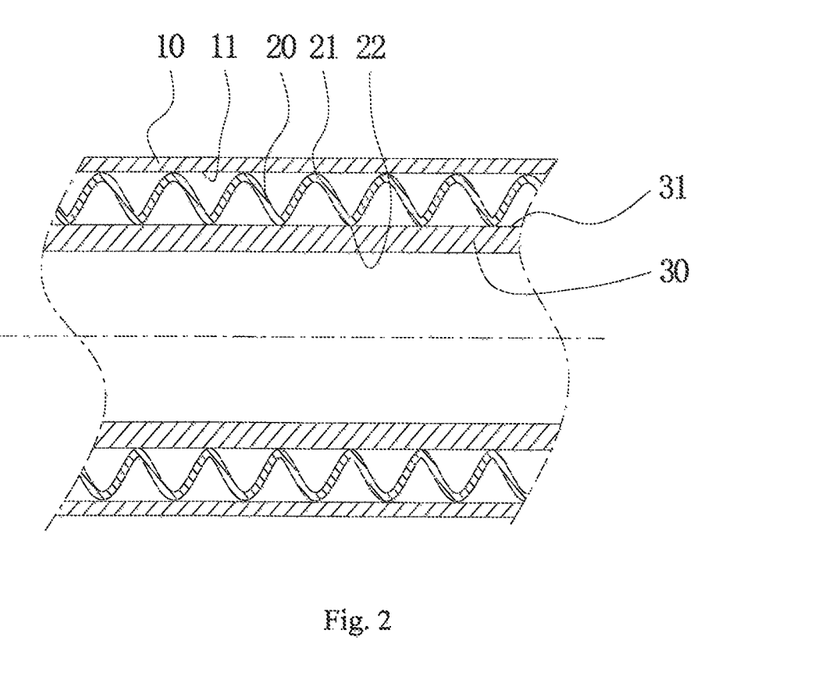
FIG. 2 is an axial sectional view of the water pipe according to one embodiment of the present disclosure.

FIGS. 1 and 2 schematically show an embodiment of a wear-resistant multi-layer retractable water pipe of the present disclosure. FIG. 1 is a transverse sectional view of the wear-resistant multi-layer retractable water pipe, and FIG. 2 is an axial sectional view of the wear-resistant multi-layer retractable water pipe. As shown in the figures, the wear-resistant multi-layer retractable water pipe includes a fabric sleeve 20 and a retractable inner pipe 30 nested therein. The fabric sleeve 20 is in turn nested in a retractable wear-resistant protective layer 10, and is configured as a one- or two- or three- or four- or multi-layer retractable corrugated fabric sleeve. An inner wall surface 11 of the wear-resistant protective layer 10 is fit with an outer surface 21 of a peak of the fabric sleeve 20. An outer bottom surface 22 of a valley of the fabric sleeve 20 is axially slidable on an outer surface 31 of the inner pipe 30 when the fabric sleeve 20 is deployed or retracted.

Since both the wear-resistant protective layer 10 and the fabric sleeve 20 are retractable, the wear-resistant protective layer 10 can be deployed or retracted along with the fabric sleeve 20 under the effect of water pressure. Since the fabric sleeve 20 is corrugated, its extension length is related to its overall length after deployment. Therefore, the inner pipe 30 and the wear-resistant protective layer 10 are elongated synchronously with the elongation of the fabric pipe 20 and are limited by the overall length of the fabric sleeve 20.

All the layers of the fabric sleeve 20 are braided into a one-piece structure or are formed by mutually knitting the single-layer structures which are braided independently. Because the longitudinally and transversely braided warp and weft threads or cross braided diagonal threads of the fabric sleeve 20 are not elastic, the maximum inner diameter and the maximum length of the fabric sleeve 20 are fixed values. It improves the pressure resistance of the entire retractable water pipe and protects the inner pipe 30 from being burst by excessive pressure.

Figure 3:
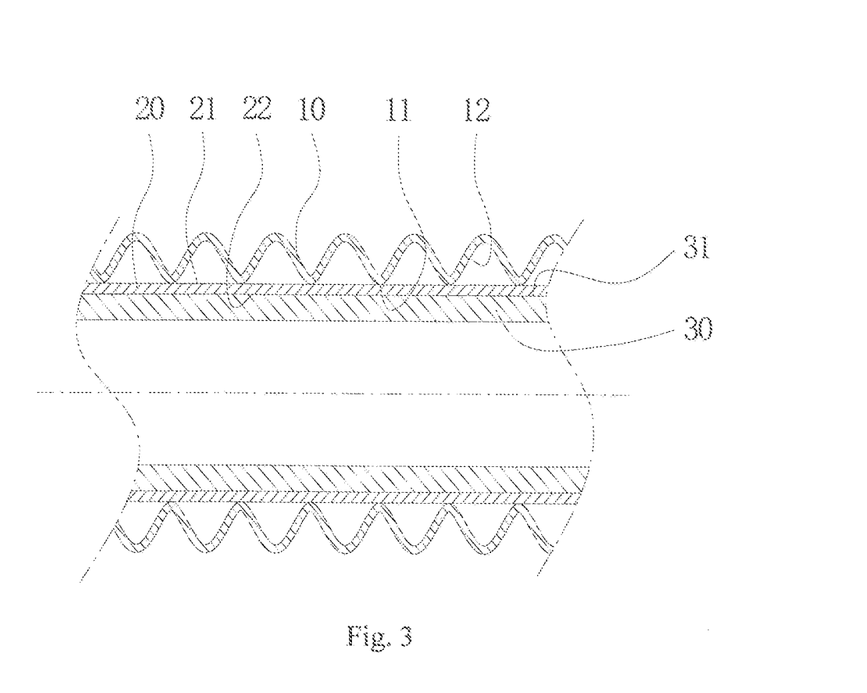
FIG. 3 is an axial sectional view of the water pipe according to another embodiment of the present disclosure, in which an inner wall surface of a wear-resistant protective layer is fit with an outer surface of a fabric sleeve.

FIG. 3 shows another embodiment of the wear-resistant multi-layer retractable water pipe. Referring to FIG. 3, the inner wall surface 11 of the wear-resistant protective layer 10 is fit with the outer surface 23 of the fabric sleeve 20, and both the wear-resistant protective layer 10 and the fabric sleeve 20 are a kind of corrugated retractable pipe.

Figure 4:
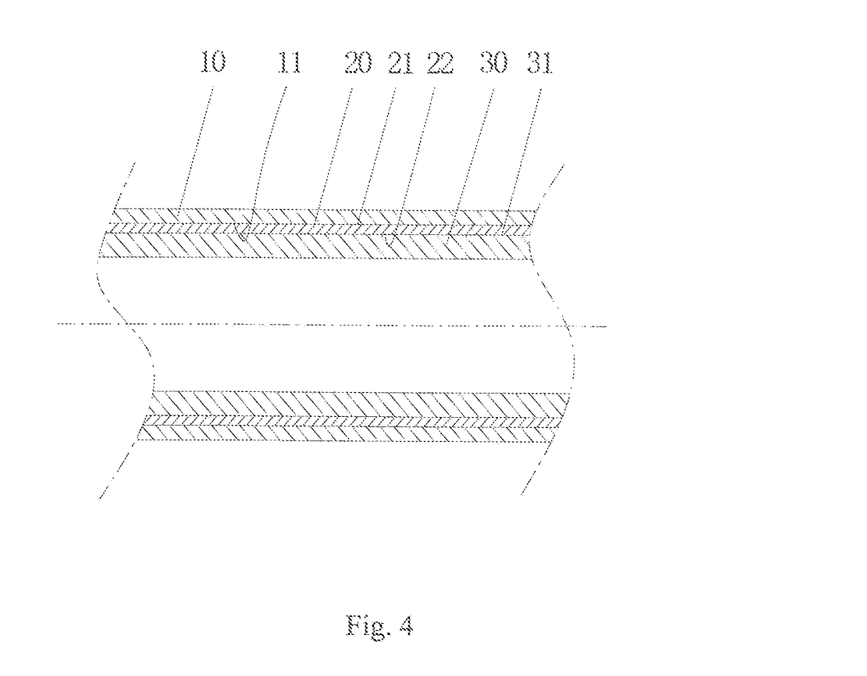
FIG. 4 is an axial sectional view of the water pipe according to a further embodiment of the present disclosure, in which an inner pipe, the fabric sleeve, the wear-resistant protective layer are respectively of straight cylindrical shape and are fit with each other.

FIG. 4 shows an axial sectional view of the wear-resistant multi-layer retractable water pipe, in which the inner pipe, the fabric sleeve, and the wear-resistant protective layer are respectively of straight cylindrical shape and are fit with each other. In this way, the inner pipe, the fabric sleeve, and the wear-resistant protective layer are deployed and retracted synchronously, thereby effectively reducing the mutual friction among the layers of the water pipe.

In some embodiments, two ends of the above-described wear-resistant multi-layer retractable water pipe are respectively connected to a pipe fitting. Accordingly, two ends of the inner pipe 30, of the fabric sleeve 20, and of the wear-resistant protective layer 10 are respectively fixed to the pipe fittings. The above-described inner pipe 30 is made of one or two or more retractable materials selected from latex, silica gel, TPE, TPR, TPU and TPX. The above-described fabric sleeve 20 is a corrugated or straight cylindrical fabric sleeve woven with chemical fiber threads, cotton threads or silk threads. The above-described wear-resistant protective layer 10 is made of a plastic material or a leather material.

In a specific embodiment, the wear-resistant multi-layer retractable water pipe may be further configured as a water pipe for hydrogen-rich water. In particular, an electrolytic connector 3 and an electrode plate 4 may be disposed between the pipe fitting and the end of the inner pipe 30, of the fabric sleeve 20, and of the wear-resistant protective layer 10, to be connected to the pipe fitting.

Figure 5:
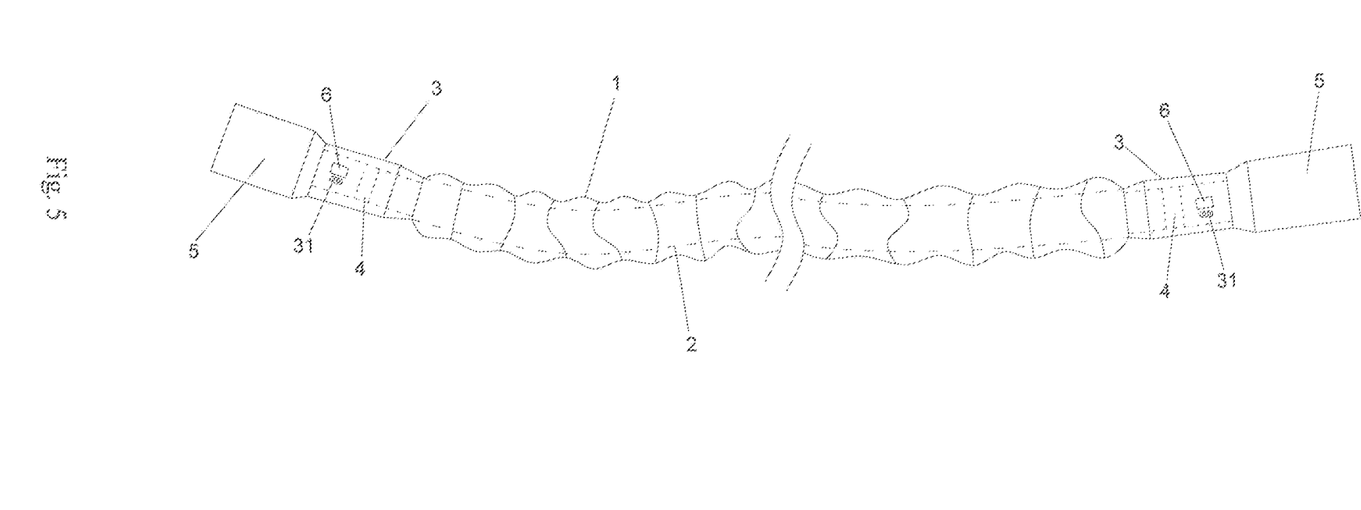
FIG. 5 is a schematic structural view of a water pipe according to one embodiment of the present disclosure, in which a hydrogen-rich water function is added to a wear-resistant multi-layer retractable water pipe.
Figure 6:
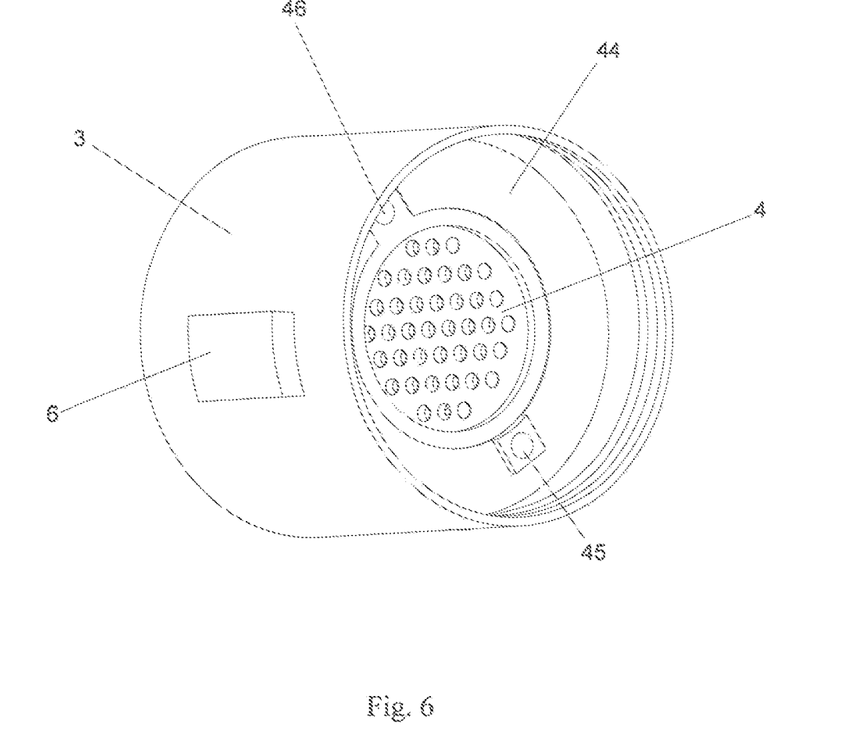
FIG. 6 is a schematic structural view of an electrolytic connector in the embodiment shown in FIG. 5.

FIGS. 5 and 6 show an embodiment of a wear-resistant multi-layer retractable water pipe for hydrogen-rich water. As shown in FIG. 5, in this embodiment, the number of the electrolytic connectors 3 is three, and the three electrolytic connectors 3 are uniformly distributed on the fabric sleeve 20. For example, the left end of the fabric sleeve 20, the left end of the inner pipe 30 and the left end of the wear-resistant protective layer 10 are fixed together and are installed on a first electrolytic connector 3, in particular via a collar; the right end of the fabric sleeve 20, the right end of the inner pipe 30 and the right end of the wear-resistant protective layer 10 are also fixed together and are installed on a second electrolytic connector 33, in particular via a collar; a third electrolytic connector 3 (not shown) is also installed at the middle of the water pipe, and the third electrolytic connector divides the wear-resistant protective layer 10, the fabric sleeve 20 and the inner pipe 30 into two sections from the middle. That is, the end of each section is mounted on the third electrolytic connector 3. As shown in FIG. 5, the water in the inner pipe 30 may flow passing the electrolytic connector 3. In other embodiments, the number of the electrolytic connectors 3 can also be two, which are respectively installed at two ends of the water pipe. In other embodiments, the number and arrangement of the electrolytic connectors 3 may vary according to the length of the water pipe, watering requirements, and the like.

As shown in FIG. 6, an electrode plate 4 is mounted in the electrolytic connector 3 and it can electrolyze the water in the inner pipe 30. In this embodiment, the electrode plate 4 is fixed in the inner hole of a snap plate 44, the latter is snapped in the inner cavity of the electrolytic connector 3, the snap plate 44 is arranged perpendicularly to the water flow channel of the electrolytic connector 3, so that the electrolytic efficiency of the water by the electrode plate 4 can be improved. In other embodiments, the electrode plate 4 may be directly installed in the inner cavity of the electrolytic connector 3, and the electrode plate 4 is arranged perpendicularly to the water flow channel of the electrolytic connector 3.

As shown in FIG. 6, an anode terminal 45 and a cathode terminal 46 are provided on the snap plate 44. The anode terminal 45 and the cathode terminal 46 are electrically connected to the electrode plate 4. A waterproof wire is led from the anode terminal 45 and the cathode terminal 46, respectively. The anode terminal 45 and the cathode terminal 46 are connected through the waterproof wires to the power source (which may be an external or internal power source).

Figure 7:
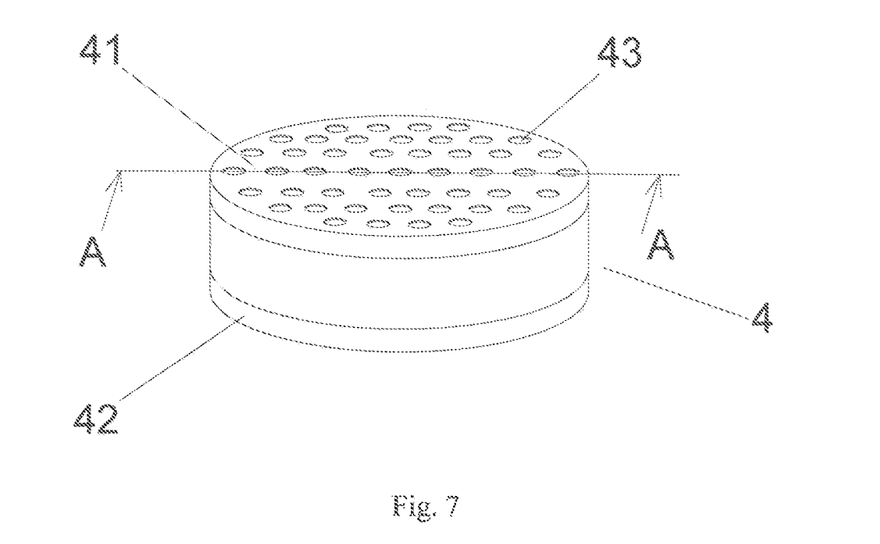
FIG. 7 is a schematic structural view of an electrode plate in the electrolytic connector shown in FIG. 6.
Figure 8:
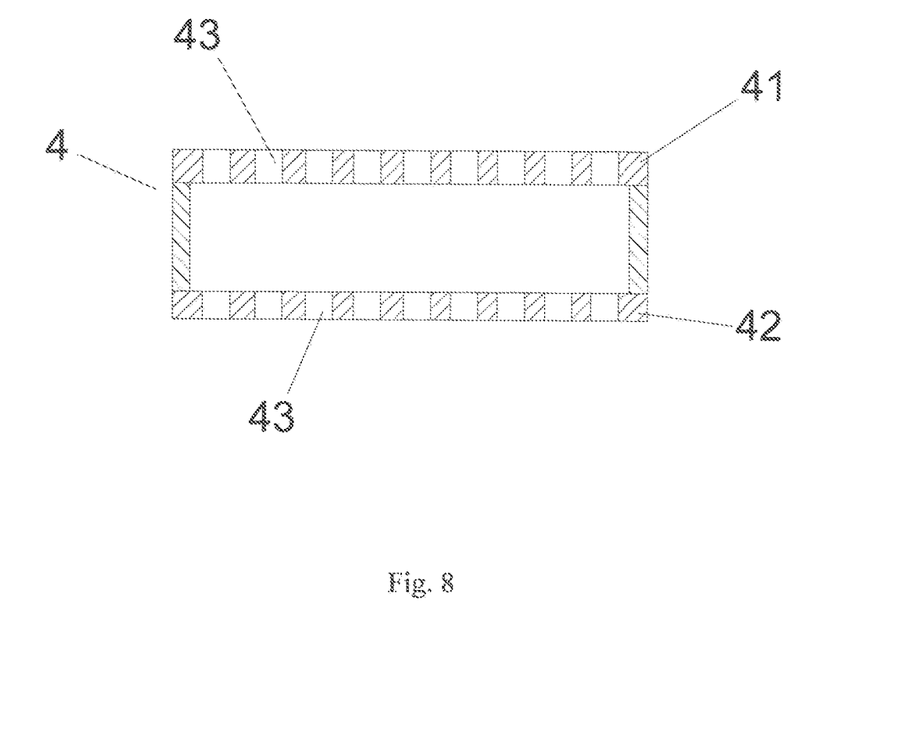
FIG. 8 is a sectional view of the electrode plate shown in FIG. 7 along the direction A-A.

As shown in FIGS. 7 and 8, the electrode plate 4 includes a cathode plate 41 and an anode plate 42 which are arranged in parallel. The gap between the periphery of the cathode plate 41 and that of the anode plate 42 is covered with an insulating material. The anode terminal 45 is electrically connected to the anode plate 42, and the cathode terminal 46 is electrically connected to the cathode plate 41. The cathode plate 41 can attract $H^+$ in the water to generate hydrogen, and the generated hydrogen enters the water in the inner pipe 30 to form the hydrogen-rich water. The hydrogen-rich water is easy to enter the cell passages of flower plants and participate in metabolism. The hydrogen-rich water can regulate the synthesis of endogenous hormones in flower plants, promote the growth of flower plants and improve the soil. The hydrogen-rich water can thanks to its bactericidal effect replace part of pesticides, but also can improve the pest resistance of flower plants. The oxygen generated on the anode plate 42 can increase the oxygen content in the water, thus providing the plants with the oxygen required for their breathing at night.

As shown in FIGS. 7 and 8, a plurality of holes 43 are formed in the cathode plate 41 and the anode plate 42 respectively. The holes 43 allow passage of the water in the inner pipe 30, while the cathode plate 41 and the anode plate 42 electrolyze the water.

As shown in FIG. 6, the inner cavity of the electrolytic connector 3 has a circular cross section, and the snap plate 44 also has a circular shape. The outer diameter of the snap plate 44 is matched with the inner diameter of the inner cavity of the electrolytic connector 3, and the snap plate 44 is snapped in the inner cavity of the electrolytic connector 3. In other embodiments, the cross-section of the inner cavity of the electrolytic connector 3 may also be square, oval, or the like, as long as the shape and size of the snap plate 44 can be matched with the dimension of the inner cavity of the electrolytic connector 3 to ensure that the flowing water entirely passes through the holes 43 in the cathode and anode plate 41, 42, thus improving the electrolytic efficiency of the water by the electrode plate 4. In other embodiments, the cathode plate 41 and the anode plate 42 may be of other shapes, such as square, and the shape of the inner hole of the corresponding snap plate 44 is also square to ensure that the cathode plate 41 and the anode plate 42 can be rightly snapped in the inner hole of the snap plate 44.

As shown in FIG. 5, in this embodiment, the left electrolytic connector 3 is mounted on one pipe fitting 5 (by means of threaded connection, plug-in interference fit connection etc.), and the right electrolytic connector 3 is also mounted on one pipe fitting 5 (by means of threaded connection, plug-in interference fit connection etc.). The pipe fitting 5 can realize the quick connection between the water pipe and a faucet or a spray gun, which is convenient, fast and labor-saving. In other embodiments, the left electrolytic connector 3 may be mounted on one pipe fitting 5, and the right electrolytic connector 3 may be directly fixed on the spray gun (by means of threaded connection, plug-in interference fit connection etc.). When used, the pipe fitting 5 can be directly connected to the faucet.

In this embodiment, one end of the electrolytic connector 3 is connected through a collar structure to the wear-resistant protective layer 10, the fabric sleeve 20 and the inner pipe 30. The other end of the electrolytic connector 3 may be formed with an internal thread or an external thread, and the electrolytic connector 3 is connected with the pipe fitting 5 through the threaded structure. In other embodiments, the electrolytic connector 3 can also be connected with the pipe fitting 5 through a plug-in interference fit structure.

As shown in FIG. 5, the left end of the wear-resistant protective layer 10, the left end of the fabric sleeve 20 and the left end of the inner pipe 30 are connected through an electrolytic connector 3 to one pipe fitting 5, and the right end of the wear-resistant protective layer 10, the right end of the fabric sleeve 20 and the right end of the inner pipe 30 are connected through an electrolytic connector 3 to another pipe fitting 5.

In addition, the water pipe for watering flowers with hydrogen-rich water may further include a power module 6. As shown in FIG. 5, in this embodiment, the power module 6 is mounted on the electrolytic connector 3. The power module 6 is electrically connected through a waterproof wire to the anode terminal 45 and the cathode terminal 46. The power module 6 supplies electrolytic current to the cathode plate 41 and the anode plate 42.

As shown in FIG. 5, in this embodiment, the power module 6 adopts a rechargeable battery. When the hydrogen-rich water is needed to water flowers, the external power line is not required, so this is very convenient. The electrolytic connector 3 is provided with a charging jack. When flower watering is not performed, the rechargeable battery can be fully charged through the charging jack. The rechargeable battery is provided with an operating switch for controlling the electrolysis of the electrode plate 4 or stopping the electrolysis. In other embodiments, the power module 6 can also be waterproofly integrated inside the electrolytic connector 3. In other embodiments, the electrode plate 4 may also be directly connected to the external power line, or the socket of the power line may be installed on the electrolytic connector 3. When the electrolysis of water is required by the user, one end of the power line is inserted directly into the socket on the electrolytic connector 3. The plug of the power line is connected to the external power socket to provide power to the electrode plate 4. When the electrolysis of water is not required, the power line is not installed.

As shown in FIG. 5, when flower watering is performed using the water pipe for hydrogen-rich water of the present disclosure, one pipe fitting 5 is mounted on the faucet and the spray gun is mounted on another pipe fitting 5. The faucet is turned on, while the electrode plate 4 is energized (by pressing the switch on the electrolytic connector 3), the cathode plate 41 and the anode plate 42 in the electrolytic connector 3 can electrolyze the water in the inner pipe 30. The cathode plate 41 can attract $H^+$ in the water to generate hydrogen, and the generated hydrogen enters the water in the inner pipe 30 to form the hydrogen-rich water. The hydrogen-rich water is easy to enter the cell passages of flower plants and participate in metabolism. The hydrogen-rich water can regulate the synthesis of endogenous hormones in flower plants, promote the growth of flower plants and improve the soil. The hydrogen-rich water can thanks to its bactericidal effect replace part of pesticides, but also can improve the pest resistance of flower plants. The oxygen generated on the anode plate 42 can increase the oxygen content in the water, thus providing the plants with the oxygen required for their breathing at night. The flower watering operator can also turn off the power module 6 according to the need, so that the water is not electrolyzed.

Figure 9:
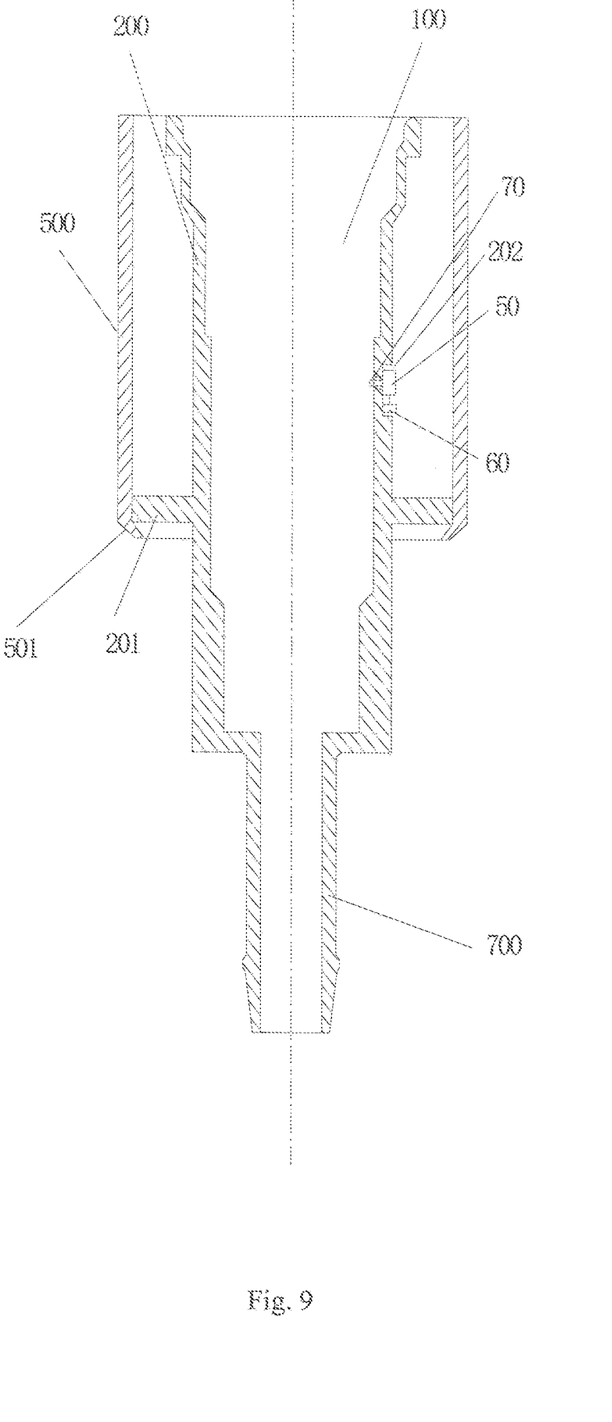
FIG. 9 is a schematic sectional structural view of a pipe fitting according to an embodiment of the present disclosure.

In specific implementation, the above-mentioned pipe fittings can be selected from the existing pipe fittings and intelligent pipe fittings. FIG. 9 shows a sectional structure of an intelligent pipe fitting. As shown in FIG. 9, the pipe fitting includes a main body 200 with a central hole 100, wherein a housing 500 is sleeved on an upper portion of the main body 200, the lower portion of the main body 200 is provided with a plug-in portion 700 of the water pipe, the top end of the central hole 100 is a reaming hole, facilitating the insertion of the spray gun or the faucet. The method for connecting the main body through the reaming hole to the spray gun or the faucet and the method for connecting the plug-in portion 700 to the water pipe can be carried out with reference to the prior art, which is not limited by the embodiments of the present disclosure. The intelligent pipe fitting provided by the embodiments of the present disclosure can increase the fun for the watering work, enhance the user experience and provide the value-added services to the user through the detection of some data, thus achieving, for example, the effects of assisting in improving the life of the water pipe, providing reasonable amount of watering, water flow and water pressure, and the like. To achieve this, those skilled in the art should understand that the pipe fitting in the specific embodiments may be any structure provided with this basic structure (that is, having a receiving cavity for mounting the control module). Therefore, the embodiments of the present disclosure are not to be construed as limiting the structure of the pipe fitting. Any other pipe fittings capable of realizing various structures for mounting the intelligent module on the pipe fitting to realize the intelligent function of the pipe fitting are regarded as an improvement based on the concept of the present disclosure.

In order to achieve the purpose of the present disclosure, the embodiments of the present disclosure may be so configured that, first a receiving cavity is provided between the main body 200 and the housing 500, and the control module and the power module are provided in the receiving cavity, wherein the control module is connected to the power module, and the power module provides independent power for the control module (in other embodiments, the power module may not be necessary, but a power line connected to the external power source is provided to supply energy). The receiving cavity may be a space formed, after the housing 500 is sleeved on the main body 200, between the both, or may be a depression provided on the sidewall of the housing 500 or of the main body 200. In the former case, the control module and the power module may be directly disposed on the sidewall of the main body 200 or of the housing 500 (the disposed control module and power module protrude from the sidewall of the main body 200 or of the housing 500 but within the receiving cavity), while in the latter case, the control module and the power module are disposed in the depression (not between the main body 200 and the housing 500, the control module and the power module should better be such arranged that they do not protrude out of the opening of the depression, thereby reducing the friction to the control module and the power module in case of the possible relative movement of main body and the housing). As shown in FIG. 9, the receiving cavity is provided as a depression 202 located on the sidewall of the main body 200, and the control module 50 and the power module 60 are disposed on the sidewall of the depression 202. As shown in FIG. 9, a water flow sensor 70 for detecting the water flow velocity is also provided at an inner surface (i.e. on a sidewall facing the central hole 100) of the main body 200 and at a position corresponding to the control module 50 inside the depression 202. The water flow sensor 70 is connected to the control module 50. The control module 50 is provided with a voice playing unit, and an audio file is stored in the control module 50. The water flow sensor 70 detects a water flow velocity signal and outputs the signal to the control module 50. The control module 50 performs the determination according to the received water flow velocity signal. If the water flow velocity signal is a non-zero value, it indicates that the pipe fitting is in use. At this time, the control module 50 outputs an audio control signal (which may be an audio signal, for example) to the voice playing unit or directly outputs the audio file to the voice playing unit. The voice playing unit plays the audio file, thus achieving automatic music play when the pipe fitting is in use. When the water flow velocity signal received by the control module 50 becomes into zero, it indicates that the use of the pipe fitting has ended. In this case, the control module 50 outputs a control signal for stopping the playing (for example, it may be an electrical signal) to the voice playing unit, and the voice playing unit stops playing the audio file according to the control signal. In addition, in a specific embodiment, a cover may also be arranged for the depression 202 to achieve a better waterproof effect.

It should be noted that, in this embodiment, the control module 50, the voice playing unit and the power module 60 may all be achieved by the existing products. For example, the control module may be achieved by a single chip microcomputer or an MCU chip or the like, the voice playing unit may be achieved by a speaker, and the power module is a battery or the like. In a specific embodiment, the housing 500 can be removably sleeved on the main body 200 to facilitate the maintenance of the control module, of the voice playing unit and of the power module. For example, as shown in FIG. 9, the protrusion 201 is formed on the outer sidewall of the main body 200, and an abutment 501 is provided at the lower end of the housing 500, in this way, after the housing 500 is sleeved on the main body 200, the housing 500 may be fixed with the main body 200 by the cooperation of the protrusion 201 and the abutment 501. In some embodiments, the abutment 501 may be made of a resilient material to facilitate the mounting and removal.

In this embodiment, the water flow sensor 70 may be connected to the control module 50 through a routing hole (with a wire therein) provided on the sidewall of the main body 200, and the routing hole may be sealed by a sealing ring to achieve a good sealing and waterproof effect.

Figure 10:
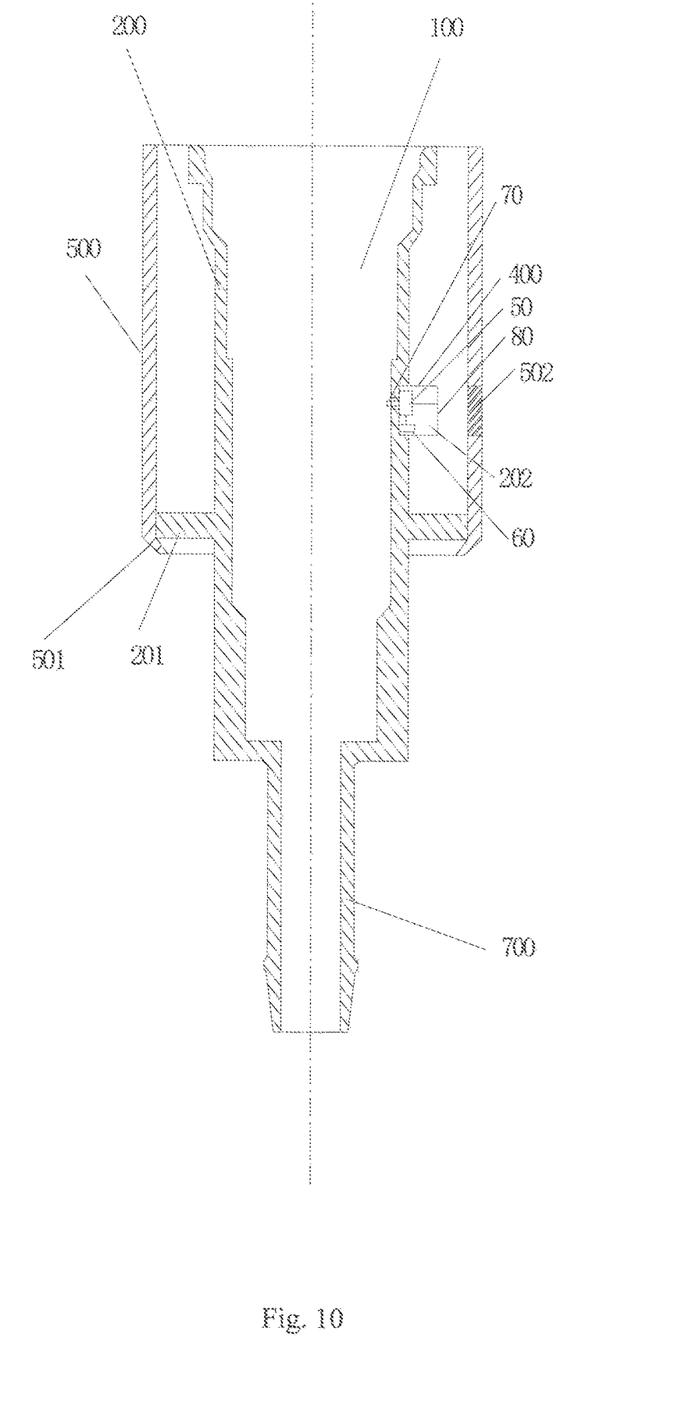
FIG. 10 is a schematic sectional structural view of a pipe fitting according to another embodiment of the present disclosure.

FIG. 10 shows an intelligent water pipe fitting according to another embodiment. In this embodiment, the depression 202 is disposed on the sidewall of the main body 200, and a display screen 80 is installed at an opening of the depression 202 (for example, the display screen may be mounted via a support structure 400, so that a space formed between the depression and the display screen is large enough). The display screen 80 is connected to the control module 50. Accordingly, in order to make the display screen visible to the user, a display window 502 is provided at a section of the housing 500 corresponding to the display screen 80. The display window 502 is made of a transparent material. In this way, the information displayed on the display screen 80 can be seen through the display window 502 on the housing. This designed structure allows an easy installation of the display screen and a simple line structure within the connector. That is, the display screen 80 can be easily connected to the control module 50 without any additional routing structure. Moreover, the protection provided by the housing 500 also renders the display screen less susceptible to damage. In the control module 50 is also stored the cross-sectional area of the section of the central hole, where the water flow sensor 70 is located (since the water flow sensor 70 is disposed on the inner sidewall of the main body 200, it is correspondingly located on the circumference of the central hole 100, and the central hole 100 has one section corresponding to the plane in which the sensor 70 is located). When the control module 50 receives the water flow velocity signal from the water flow sensor 70 and determines that the water flow velocity signal changes from zero to non-zero, the control module 50 records the start time T1 and stores the received real-time water flow signal. When the control module 50 determines that the water flow velocity signal changes from non-zero to zero, the control module 50 records the end time T2, and uses the stored real-time water flow velocity signal for this time period T1-T2 to calculate the water flow. That is, the control module 50 calculates the average value of the water flow velocity within this time period, and calculates a water consumption for working, e.g. flower watering, during the period of time by using the average value of the water flow velocity, the start time T1, the end time T2, and the cross-sectional area of the section of the central hole at which the water flow sensor 70 is located, and outputs the water consumption to the display screen 80 for display. The calculation method can be implemented by the formula: water consumption=water flow velocity x cross-sectional area×(T2−T1). Through the calculation and display of water consumption, it is possible for a user to visibly observe the amount of water consumed by this work, so that the user can not only read the energy consumption but also control the water consumption according to the actual demand, for example, during the work of flower watering. The user can quantitatively water the flowers according to the weather and the demand of each of flowers on water consumption, so as to achieve the effect of promoting the growth of plants or flowers. In a preferred embodiment, the calculation and display of water consumption may be real-time, that is, the calculation and output display may be performed immediately when a new water flow velocity signal is obtained. For example, when the control module 50 determines that the latest water flow velocity signal received is continuously non-zero, the real-time latest end time T2 is recorded, and the calculation and output display of water consumption is performed. This is more convenient for the user to consume the water according to the demand. In other embodiments, in order to improve the accuracy of the calculation result, a plurality of water flow sensors may be provided. For example, the plurality of water flow sensors may be evenly distributed along the same cross-section and respectively connected to the control module. The control module performs an average value calculation based on the information detected by the plurality of water flow sensors to obtain the average water flow velocity detected by the plurality of water flow sensors, and uses the average water flow velocity as a basis for calculating the water consumption. That is, when the calculation is performed, the determination of the start time and the end time is made on the basis of the average values from the plurality of water flow sensors, and the water consumption is calculated based on the average value of the plurality of record values during the timing period (that is, two averages are performed, one is the average among the data measured by the plurality of sensors, and the other is the average of all the recorded values during the timing period). In examples where a plurality of water flow sensors are provided, the control of music playing by the control module may be based on a determination of the average water flow velocity, that is, when the average water flow velocity is non-zero, the audio file is output to the audio playing unit. When a plurality of water flow sensors are provided, the depression 202 may be provided as a circular depression along the outer circumference of the main body 200. A plurality of water flow sensors may be evenly distributed along the inner sidewall (i.e. the sidewall near the central hole) of the circular depression. The connection to the control module 50 may be so configured that routing holes are formed at corresponding positions of the sensors, and a waterproof wire is extended along the circumferential surface of the depression to the control module 50, wherein each of the routing holes is provided with a sealing ring.

In other embodiments, in order to improve the accuracy of the determination of whether the state is a working state or not, a preset threshold may also be stored in the control module. The control module judges whether the water flow velocity signal exceeds the threshold to start the timer. That is, if the water flow velocity signal exceeds the threshold, then it is determined that the work is started, the start time T1 is recorded, and thereafter the end time T2 is obtained by determining whether it continues to be greater than the threshold.

It should be noted that in the embodiment where the water flow sensor 70 detects the water flow velocity signal, the above function can be realized by a determination of the control module 50 on the received water flow velocity signal. When the water flow sensor detects a water flow signal other than velocity, the control module 50 may first convert the signal detected by the water flow sensor into the water flow velocity signal and then perform the above determination, wherein the method for converting the signal detected by the water flow sensor into the water flow velocity signal can be implemented with reference to the prior art, which is not described in the embodiments of the present disclosure.

Figure 11:
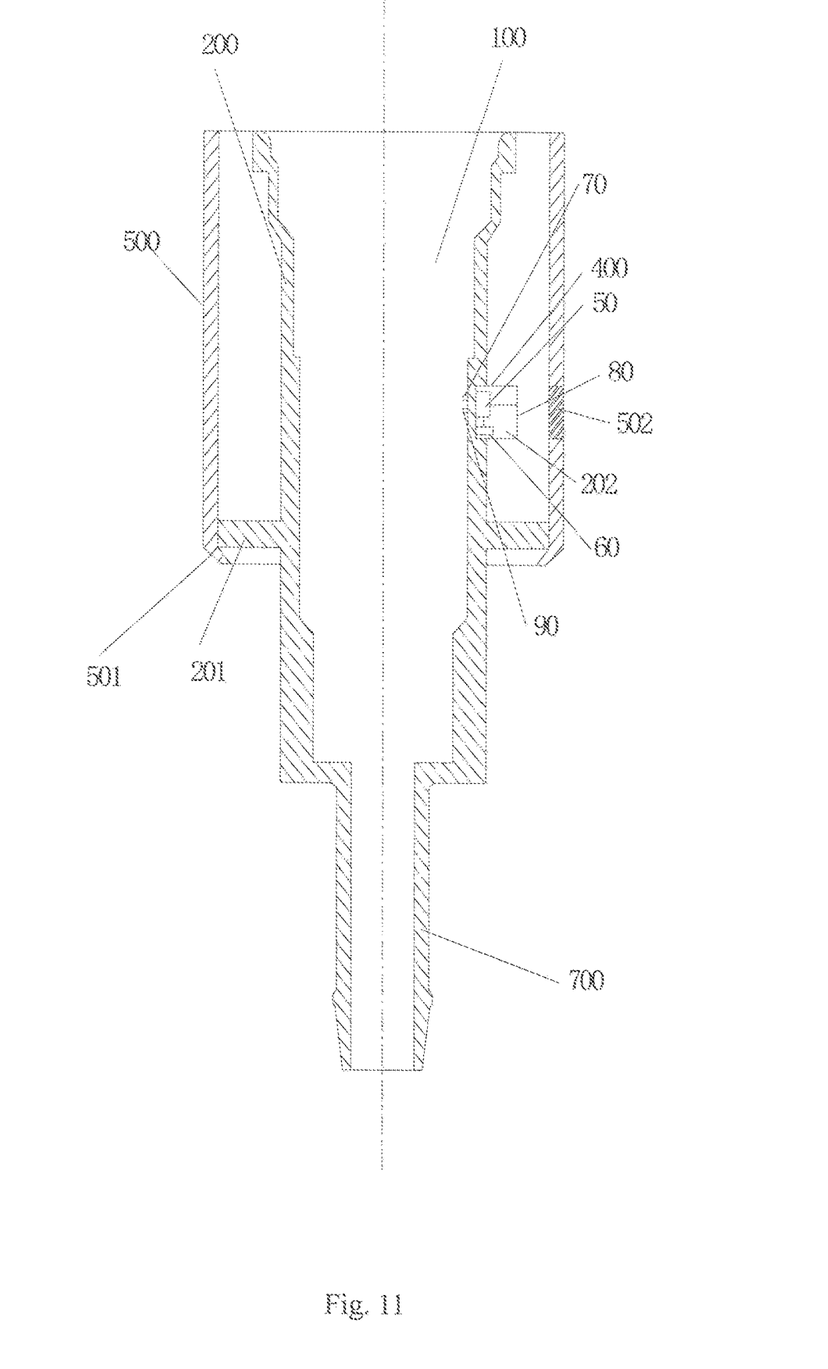
FIG. 11 is a schematic sectional structural view of a pipe fitting according to a further embodiment of the present disclosure.

FIG. 11 shows an intelligent water pipe fitting according to a further embodiment of the present disclosure. As shown in FIG. 11, in this embodiment, a pressure sensor 90 is further disposed on a sidewall of the main body 200 near the central hole 100, wherein the pressure sensor 90 is connected to the control module 50 for detecting a water pressure and outputting it to the control module 50, and the control module 50 outputs the water pressure to the display screen 80 for display. The pressure sensor 90 may be disposed in a similar manner to the water flow sensor 70, for example, a plurality of pressure sensors are evenly distributed on the sidewall of the depression 202. The control module 50 can obtain the real-time water pressure output by calculating the pressure average values measured by the plurality of pressure sensors 90. The control of playing audio file by the control module 50 may also be based on the pressure signal output by the pressure sensor 90. That is, when the pressure signal is non-zero or exceeds a certain threshold (which can be preset and stored in the control module), the audio file is output to the audio playing unit for audio playing. Further, the control of the audio playing may also be based on the determination of the water flow signal output by the water flow sensor 70 along with the pressure signal output by the pressure sensor 90, that is, the playing is performed only when the both satisfy certain conditions. This guarantees the accuracy of playing the audio file upon working.

The intelligent pipe fitting provided by the embodiments of the present disclosure can be applied to different water pipes. That is, as long as the pipe fitting provided by the embodiments of the present disclosure is connected to a water pipe, this water pipe can be intelligentized. As a specific embodiment, the specific application object is the above wear-resistant multi-layer retractable water pipe. In this way, music can be played while watering flowers, and statistics and display of water pressure, water consumption, and human energy consumption can also be realized. This facilitates the user to perform the adjustment of water flow and water consumption or arrange the exercise, based on the actual needs of water pressure, water consumption, and human energy consumption. In addition, the deployment or retraction of the retractable water pipe relies on the deformation of the elastic inner pipe under the effect of water pressure. Considering the inner pipe will become thinner under the water pressure, the water faucet may be controlled through monitoring the water pressure and/or according to the demand, so that the insufficient deployment (due to a small water pressure) or the excessive deployment (which may cause a broken of the inner pipe due to an over pressure) may be avoided.

The above description only refers to some embodiments of the present disclosure. For a person of ordinary skill in the art, several variations and improvements may be made without departing from the concept of the present disclosure, and these are all within the protection scope of the present disclosure.

What is claimed is:

1. A wear-resistant multi-layer retractable water pipe, comprising:
   a retractable inner pipe;
   a fabric sleeve, configured as a one- or multi-layer retractable fabric sleeve; and
   a retractable wear-resistant protective layer,
   wherein the retractable inner pipe is nested in the fabric sleeve, and the fabric sleeve is nested in the retractable wear-resistant protective layer, and
   wherein the fabric sleeve is a corrugated sleeve forming a plurality of valleys, which are axially slidable on an outer surface of the inner pine when the fabric sleeve is deployed or retracted.

2. The water pipe according to claim 1, wherein the wear-resistant protective layer can be deployed or retracted as along with the deployment or retraction of the fabric sleeve.

3. The water pipe according to claim 1, wherein the fabric sleeve forms a plurality of peaks, which are fit with an inner wall surface of the wear-resistant protective layer.

4. The water pipe according to claim 1, wherein an inner wall surface of the wear-resistant protective layer is fit with an outer surface of the fabric sleeve.

5. The water pipe according to claim 1, wherein two ends of the water pipe are respectively connected to a pipe fitting, on which two ends of the inner pipe, of the fabric sleeve, and of the wear-resistant protective layer are respectively fixed.

6. The water pipe according to claim 1, wherein the inner pipe is made of at least one retractable material selected from latex, silica gel, TPE, TPR, TPU and TPX.

7. The water pipe according to claim 1, wherein the fabric sleeve is a corrugated or straight cylindrical fabric sleeve woven with chemical fiber threads, cotton threads or silk threads.

8. The water pipe according to any one of claims 1, 2 to 7, wherein the wear-resistant protective layer is made of a retractable plastic material or leather material.

* * * * *